US006536440B1

(12) United States Patent
Dawson

(10) Patent No.: US 6,536,440 B1
(45) Date of Patent: Mar. 25, 2003

(54) METHOD AND SYSTEM FOR GENERATING SENSORY DATA ONTO THE HUMAN NEURAL CORTEX

(75) Inventor: Thomas P. Dawson, Escondido, CA (US)

(73) Assignees: Sony Corporation, Tokyo (JP); Sony Electronics, Inc., Park Ridge, NJ (US)

( * ) Notice: Subject to any disclaimer, the term of this patent is extended or adjusted under 35 U.S.C. 154(b) by 228 days.

(21) Appl. No.: 09/690,571

(22) Filed: Oct. 17, 2000

(51) Int. Cl.[7] .............................................. A61B 19/00

(52) U.S. Cl. ....................................... 128/897; 128/898

(58) Field of Search ................................ 128/897, 898, 128/24

(56) References Cited

U.S. PATENT DOCUMENTS

| | | | |
|---|---|---|---|
| 3,848,608 A | 11/1974 | Leonard | 128/419 R |
| 4,343,301 A | 8/1982 | Indech | 128/24 |
| 4,611,596 A | 9/1986 | Wasserman | 128/419 R |
| 4,628,933 A | 12/1986 | Michelson | 128/419 R |
| 4,664,117 A * | 5/1987 | Beck | 128/897 |
| 4,883,067 A | 11/1989 | Knispel | 128/732 |
| 4,979,508 A | 12/1990 | Beck | 128/419 R |
| 5,031,154 A | 7/1991 | Watanabe | 367/8 |
| 5,097,326 A | 3/1992 | Meijer | 358/94 |
| 5,109,844 A | 5/1992 | De Juan, Jr. et al. | 128/419 R |
| 5,159,927 A | 11/1992 | Schmid | 128/419 R |
| 5,179,455 A | 1/1993 | Garlick | 359/9 |
| 5,651,365 A | 7/1997 | Hanafy et al. | 128/622.03 |
| 5,738,625 A * | 4/1998 | Gluck | 128/897 |
| 5,853,370 A | 12/1998 | Chance | 600/473 |
| 5,935,155 A | 8/1999 | Humayun et al. | 607/54 |
| 5,956,292 A | 9/1999 | Bernstein | 367/140 |
| 5,971,925 A | 10/1999 | Hossack et al. | 600/443 |
| 6,017,302 A * | 1/2000 | Loos | 600/28 |

OTHER PUBLICATIONS

Department of Electrical and Computer Engineering, University of Colorado, 1990, Richard T. Mihran, Frank S. Barnes, Howard Wachtel. "Transient Modification of Nerve Excitability in Vitro By Single Ultrasound Pulses".

Ultrasound Med Biol 1990, Department of Electrical and Computer Engineering, University of Colorado. "Temporally–specific modification of myelinated axon excitability in virto following a single ultrasound pulse" (pp. 297–309) Mihran RT; Barnes FS; and Wachtel H.

The Pennsylvaia State University, Department of Physics. 1984, J.D. Maynard, E.G. Williams, and Y. Lee. Nearfiled acoustic holography:n I. Theory of generalized holography and the development of NAH.

Department of Molecular and Cell Biology, Division of Neurobiology, University of California. Garrett B. Stanley, Fei F. Li, and Yang Dan. "Reconstruction of Natural Scenes from Ensemble Responses in the Lateral Geniculate Nucleus" The Journal of Neuroscience, pp 8036–8042; 1999.

Ultrasonics Fundamentals, Technology, Applications. Dale Ensminger, Columbus, Ohio. (pp. 373–376).

(List continued on next page.)

*Primary Examiner*—Gregory Huson
*Assistant Examiner*—Azy Kokabi
(74) *Attorney, Agent, or Firm*—Mayer Fortkort & Williams, PC; Karin L. Williams, Esq.

(57) ABSTRACT

A non-invasive system and process for projecting sensory data onto the human neural cortex is provided. The system includes a primary transducer array and a secondary transducer array. The primary transducer array acts as a coherent signal source, and the secondary transducer array acts as a controllable diffraction pattern that focuses energy onto the neural cortex in a desired pattern. In addition, the pattern of energy is constructed such that each portion projected into the neural cortex may be individually pulsed at low frequency. This low frequency pulsing is formed by controlling the phase differences between the emitted energy of the elements of primary and secondary transducer arrays.

14 Claims, 3 Drawing Sheets

OTHER PUBLICATIONS

"Human hearing in connection with the action of ultrasound in the megahertz range on the aural labyrinth" 1979. L. R. Gavrilov, G. V. Gershuni, V.I. Pudov, A.S. Rozenblyum, and E.M. Tsirul'nikov. American Institute of Phusics pp. 290–292.

The Institute of Electrical and Electronics Engineers, Inc. 1996; Richard A. Normann, Edwin M. Maynard, K. Shane Guillory, and David J. Warren. "Cortical Implants for the Blind".

Computational Neuroscience 13; Eric L. Schwartz, Bjorn Merker, Estarose Wolfson, and Alan Shaw. 1988. "Applications of Computer Graphics and Image Processing to 2D and 3D Modeling of the Functional Architecture of Visual Cortex".

CMPnet. The Technology Network. Feb. 10, 1997. "Treading fine line between man and machine, researchers pursue silicon prostheses—Chip implants: weird science with a noble purpose—Second of two parts" Larry Lange.

EETIMESonline, *www.cmpnet.com;* The Technology Network/ 1999; ;Craig Matsumoto, EE Times; ISSCC: "Papers outline biochips to restore eyesight, movement".

JN Online. The Journal of Neurophysiology, vol. 77 No. 6 1997, pp. 2879–2909, The American Physiological Society. "Encoding of Binocular Disparity by Complex Cells in the Cat's Visual Cortex".

Gttp:www.bionictech.com, Center for Neural Interfaces. Richard A. Normann, Ph.D.

BBC News Online Science, Dr. David Whithouse, Sci/Tech Computer uses cat's brain to see.

*Kksbio@engr.psu.edu*, PennState College of Engineering, The Whitaker Center for Medical Ultrasonic Transducer Engineering.

Dpmi.tu–graz.ac.at/research/BCI; Brain Computer Interface.

Ipaustralia.gov.au/fun/patents/02_ear.htm; Bionic Ear Patent; Melbourne University—Australian Patent 519851; filing date 1978.

Measurement and Projection of Acoustic Fields; Earl G. Williams; Nava Research Laboratory, Code 5137, Washing D.C. 20375.

Resonance, Newsletter of the Bioelectromagnetics Special Interest Group. pp. 11–13, 15–16. Judy Wall.

\* cited by examiner

METHOD AND SYSTEM FOR GENERATING SENSORY DATA ONTO THE HUMAN NEURAL CORTEX

CROSS REFERENCE TO RELATED APPLICATIONS

The present Application is related to the U.S. patent application entitled "Method And System For Forming An Acoustic Signal From Neural Timing Difference Data," Ser. No. 09/690,786, co-filed with the present application on even date, and assigned to the Assignee of the present invention, and is hereby incorporated by reference in its entirety.

FIELD OF THE INVENTION

The present invention relates to non-invasive methods and systems for generating sensory experiences within the human neural cortex.

BACKGROUND OF THE INVENTION

A conventional technique for generating neural activity in the human nervous system requires surgical implants. The implants may comprise wires that cause electronic impulses to interact with some portion of the human nervous system, such as the human neural cortex, and thereby cause neural activity in the human neural cortex. Researchers have successfully mapped audio sensory data to the cochlear channel, and visual data to the visual cortex.

Conventional invasive techniques have several drawbacks. First, surgical implants may cause patient trauma and medical complications during and/or after surgery. Second, additional or on-going surgery may be required, particularly if new technology is developed.

SUMMARY

The present invention solves the foregoing drawbacks by providing a non-invasive system and process for generating/projecting sensory data (visual, audio, taste, smell or touch) within/onto the human neural cortex.

One embodiment of the system comprises a primary transducer array and a secondary transducer array. The primary transducer array acts as a coherent or nearly-coherent signal source. The secondary transducer array acts as a controllable, acoustical diffraction pattern that shapes, focuses and modulates energy from the primary transducer onto the neural cortex in a desired pattern. The secondary transducer emits acoustical energy that may be shifted in phase and amplitude relative to the primary array emissions.

The pattern of energy is constructed such that each portion of the pattern projected into the neural cortex may be individually pulsed at low frequency. The system produces low frequency pulsing by controlling the phase differences between the emitted energy of the primary and secondary transducer array elements. The pulsed ultrasonic signal alters the neural firing timing in the cortex. Changes in the neural firing timing induce various sensory experiences depending on the location of the firing timing change in the cortex. The mapping of sensory areas of the cortex is known and used in current surgically invasive techniques. Thus, the system induces recognizable sensory experiences by applying ultrasonic energy pulsed at low frequency in one or more selected patterns on one or more selected locations of the cortex.

One of the advantages of the present system is that no invasive surgery is needed to assist a person, such as a blind person, to view live and/or recorded images or hear sounds.

This brief summary has been provided so that the nature of the invention may be understood quickly. A more complete understanding of the invention can be obtained by reference to the following detailed description of the preferred embodiments thereof in connection with the attached drawings.

BRIEF DESCRIPTION OF THE DRAWINGS

Use of the same reference symbols in different figures indicates similar or identical items.

DETAILED DESCRIPTION

Figure 1:
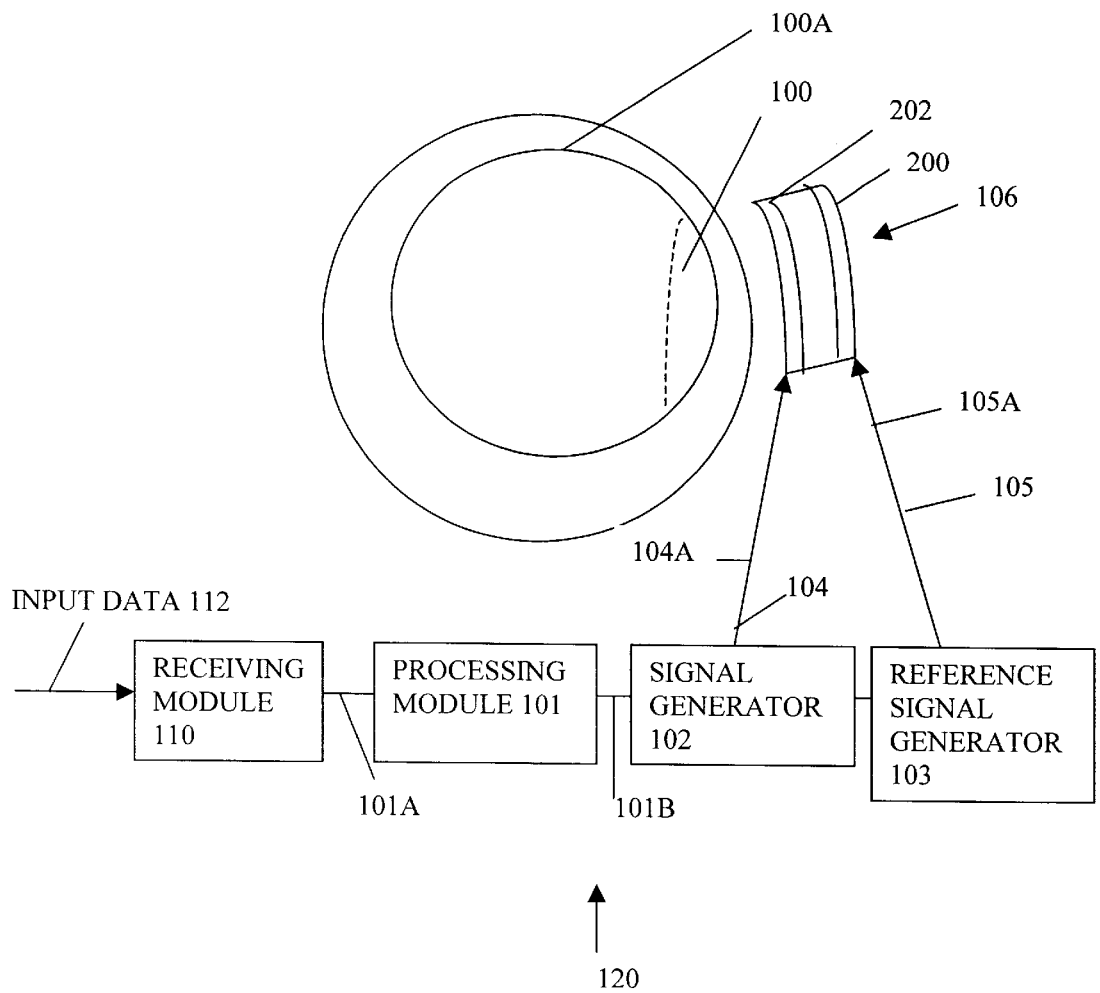
FIG. 1 illustrates one embodiment of a system in accordance with the present invention.

FIG. 1 illustrates one embodiment of a system 120 in accordance with the present invention. FIG. 1 shows a visual portion 100 of the human cortex located in a person's brain 100A, such as for example, a vision-impaired person's brain. The system 120 of FIG. 1 is used with the visual cortex 100 merely as an example and is not intended to limit the scope of the invention. Instead of or in addition to the visual cortex 100, the system 120 may be used to stimulate neural activity in other areas of the nervous system. For example, the system 120 may be used as is or modified to generate audio, taste, smell or touch sensations within the brain 100A.

In FIG. 1, the system 120 comprises a receiving module 110, a processing module 101, a signal generator 102, a reference signal generator 103, a transducer system 106, a first signal line 104 and a second signal line 105. The receiving module 110, processing module 101, signal generator 102, and reference signal generator 103, may be referred to as, alone or in combination, a sensory data processing system. Various configurations of the system 120 may be configured in accordance with the present invention. The system 120 may comprise other modules and components in addition to or instead of the modules and components shown in FIG. 1.

In general, the system 120 receives, analyzes and transfers the sensory data 112 to the human brain 100A. The receiving module 110 receives sensory input data 112. Such data 112 may comprise live video data captured by a video camera (not shown) which a vision-impaired person may not be able to see. The sensory data 112 may be live or recorded. The data 112 may be generated by other sources, such as for example a VCR, a DVD player, a cable broadcast, a satellite broadcast, an Internet connection, etc.

The processing module 101 receives input data 101A from the receiving module 110 and formats or converts the data 101A. For example, analog input data from the receiving module 110 may be digitized and/or converted into a neural firing time difference pattern. In one embodiment, the system 120 uses a technique that is reversed from a technique disclosed in "Reconstruction of Natural Scenes from Ensemble Responses in the Lateral Geniculate Nucleus" by Garrett B. Stanley et al. in the Sep. 15, 1999 issue of the Journal of Neuroscience, which is hereby incorporated by reference in its entirety.

Processed data 101B is transferred to the signal generator 102. Based upon the data 101B, the signal generator 102 generates a first signal 104A on the first line 104. The reference signal generator 103 generates a reference signal 105A on the second line 105. Both signals 104A and 105A are transferred to a transducer system 106.

Figure 2:
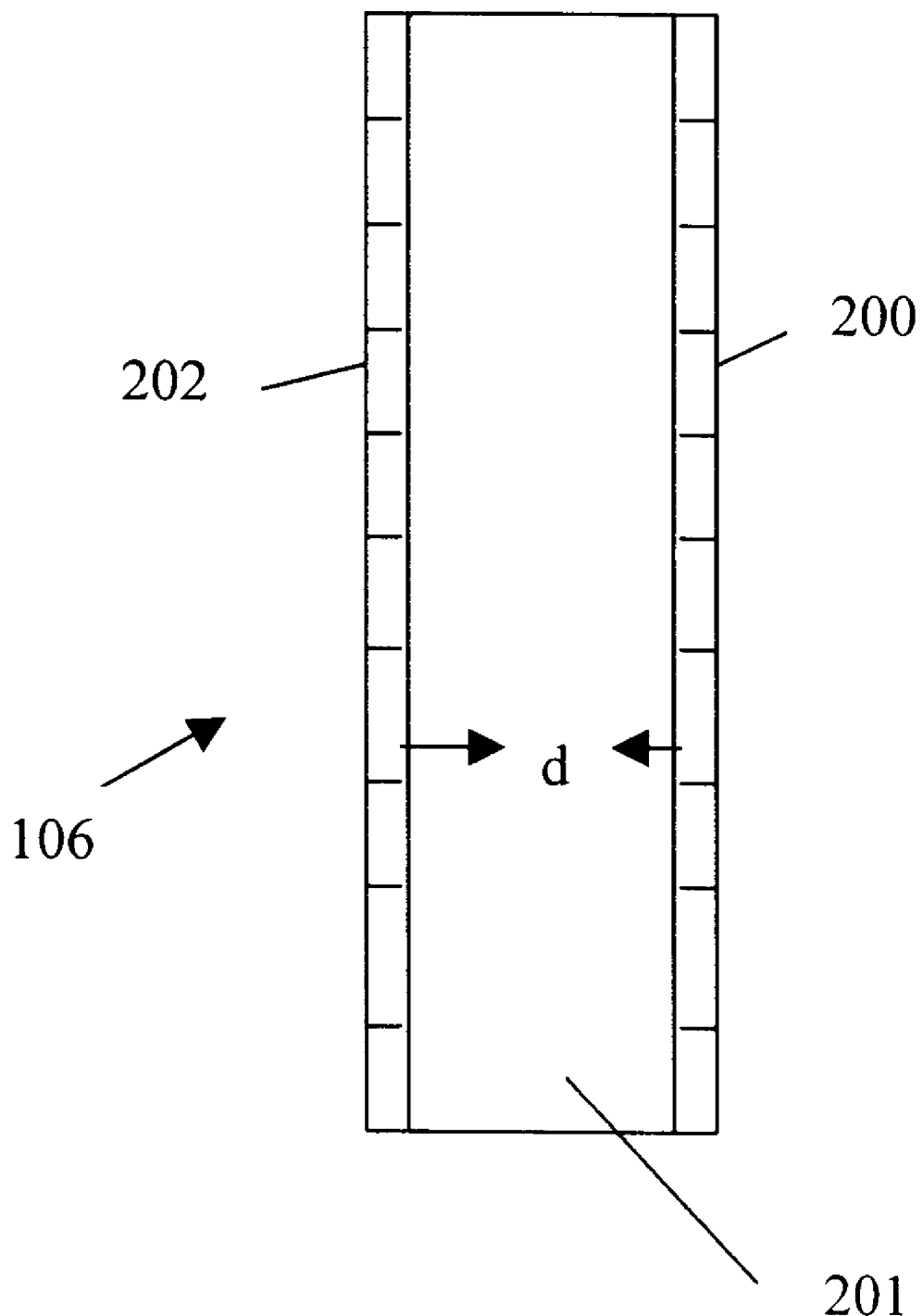
FIG. 2 illustrates one embodiment of a transducer system within the system of FIG. 1.

FIG. 2 illustrates one embodiment of a transducer system 106 within the system 120 of FIG. 1. The transducer system 106 includes a primary (or first) transducer array 200, and a secondary (or second) transducer array 202. An aperture 201 with a distance "d" separates the primary and secondary arrays 200 and 202. The distance 201 may be fixed or adjusted depending on the wavelength of energy emitted by primary array 200. In one embodiment, the distance 201 is equal to the wavelength of sound emitted by the primary transducer 200.

The primary transducer array 200 may comprise one or more columns and rows of individually-controllable piezoelectric elements. The secondary transducer array 202 may also comprise a two-dimensional array of individually-controllable piezoelectric elements.

In one embodiment, the primary and/or secondary transducer array 200, 202 each comprise a thin sheet of metal, glass, plastic or ceramic material covered with a two-dimensional array of individually-controllable piezoelectric elements. Each element in the arrays 200, 202 may emit a unique signal. The arrays 200, 202 may or may not be flat and may be shaped to conform to a portion of the human head over which the transducer system 106 lays to provide better focusing. The layout of individual elements within each array 200, 202 can also be altered to provide better focusing, according to the shape of the area of the human cortex where signal 104A is to be projected.

In one embodiment, the arrays 200, 202 comprise piezoelectric elements that are held together by a flexible material, such as plastic or rubber. This embodiment allows the arrays 200, 202 to further conform to a portion of the human head over which the transducer system 106 lays to provide better focusing.

The primary and secondary transducer arrays 200 and 202 are arranged such that the primary array 200 acts as a source of coherent energy, while the secondary array 202 acts as a programmable diffraction grating. For example, the primary transducer array 200 may comprise a phased array of emitters, whereby the combined output of some or all of the emitters appears to the secondary transducer array 202 as a coherent acoustical signal source. The primary array 200 may emit acoustical energy, thereby providing an acoustical implementation of projective holography. In one embodiment, the phase of one or more array elements in the primary array 200 is controllable to allow shaping of the energy received by the secondary transducer array 202. The primary and secondary arrays 200 and 202 may emit ultrasonic energy at the same wavelength.

The secondary transducer array 202 may comprise an array of emitters, where each emitter can be individually controlled for amplitude and phase relative to the energy emitted by primary transducer 200. Changes in signal amplitude and phase are driven by signal 104A. The secondary array 202 may provide focusing and low frequency modulation of phase differences and/or signal amplitude between the energy emitted by the arrays 200, 202. The modulation of phase differences and/or signal amplitude induces low frequency vibrations in the neurons of the visual cortex 100. The focusing effect is accomplished by the primary array 200 acting as a coherent signal source, and the secondary array 202 acting as a controllable diffraction pattern, based upon signals 104A and 105A.

Ultrasonic frequencies may accurately place signal patterns within the cortex. Interaction of emissions from the primary and secondary arrays 200, 202 projects an interference pattern (e.g., low frequency signals or pulses) in the brain 100A. The projected interference pattern creates a highly defined pattern within the visual cortex 100 or another other part of the human neural cortex. Each point in the pattern may have an individually pulsed low frequency amplitude that is used to modify neural firing times.

Low frequency amplitude modulation combined with wavelength phase interactions from the primary and secondary transducer arrays 200, 202 form a stimulus to activate neurons in the visual cortex area 100 or another other part of the human neural cortex. By controlling the pattern of signal amplitude and phase shifts in secondary array 202, a wide range of patterns can be focused towards visual cortex 100 or any other region of the human cortex. Ultrasonic signals altering neural firings are discussed in "Temporally-specific modification of myelinated axon excitability in vitro following a single ultrasound pulse" by Mihran et al. published by the Ultrasound Med Biol 1990, 16(3), pp. 297–309 and "Transient Modification of Nerve Excitability In Vitro by Single Ultrasound Pulses" by Mihran et al. found in the Department of Electrical and Computer Engineering, University of Colorado, 1990, paper #90-038, which are hereby incorporated by reference in their entirety.

Changes in the neural firing timing induce various sensory experiences depending on the location of the firing timing change in the cortex. The mapping of sensory areas of the cortex is known and used in current surgically invasive techniques.

Figure 3:
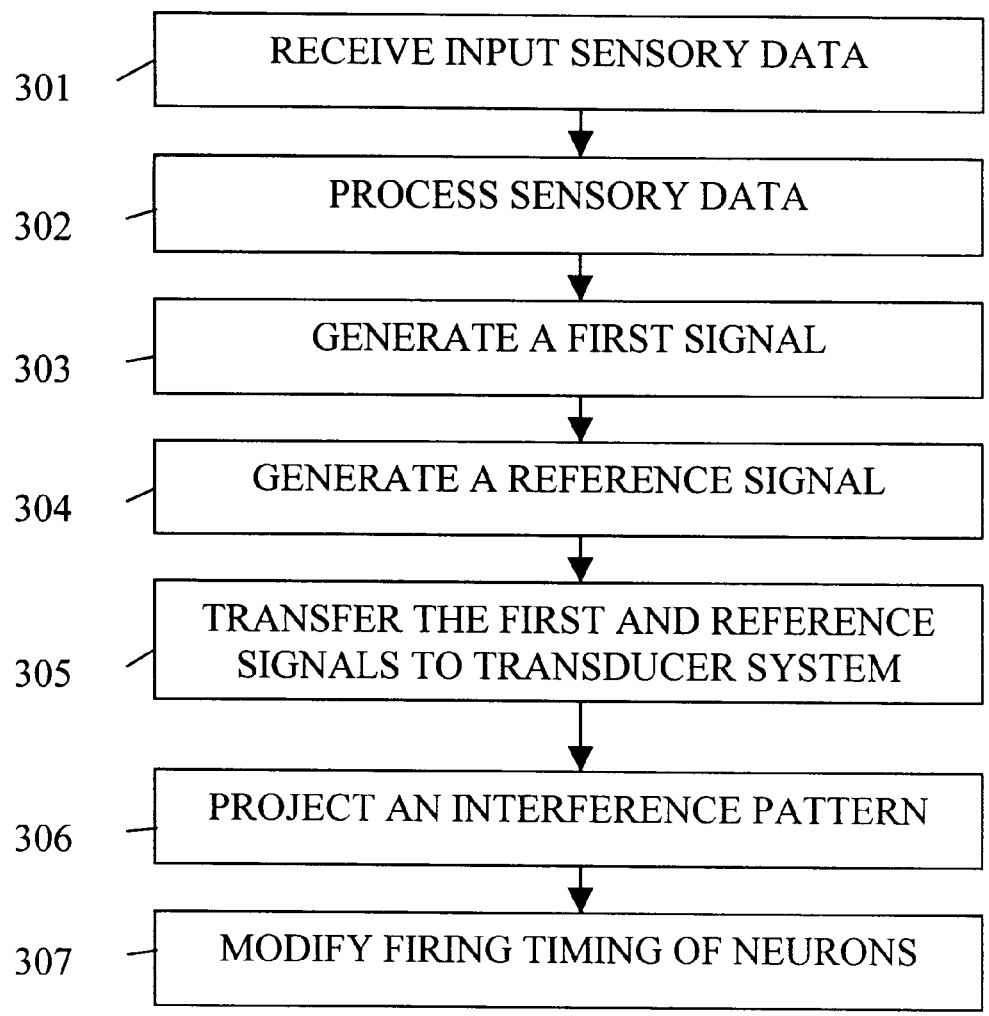
FIG. 3 illustrates one embodiment of a process in accordance with the present invention.

FIG. 3 illustrates one embodiment of a process in accordance with the present invention. In a process block 301, the receiving module 110 (FIG. 1) receives sensory input data 112 from, for example, a video camera, VCR, DVD player, cable broadcast, satellite broadcast, and/or Internet connection. The receiving module 110 outputs the data 101A to the processing module 101 (FIG. 1).

In a block 302, the processing module 101 processes the input data 101A. As stated above, in one embodiment, the processing module 101 digitizes analog data 101A from the receiving module 110 and/or converts the data 101A into a set of neural firing time differences or a pattern.

In a block 303, the signal generator 102 converts the firing time differences to a first signal 104A. For example, the first signal 104A may comprise an acoustical pattern, which comprises a plurality of amplitude and phase differences. In one embodiment, this conversion is accomplished by using known techniques in generating projective holograms. Acoustic holography is discussed in "Nearfield acoustic holography: I. Theory of generalized holography and the development of NAH" by J. D. Maynard et al. in the October 1985 issue of the Journal of the Acoustical Society of America, which is hereby incorporated by reference in its entirety.

In a block 304, the reference generator module 103 generates a reference signal 105A, which provides a coherent signal source, onto the second line 105. In one embodiment, the acts described in blocks 303 and 304 occur substantially simultaneously.

In a block 305, signals 104A and 105A are transferred to transducer system 106. The first signal 104A is transferred to the secondary array 202. The reference signal 105A is transferred to the primary array 200.

In a block 306, the transducer arrays 200 and 202 project a focused interference pattern onto the human cortex. The shape of the interference pattern and the amplitude pulse rate for each portion of the pattern may be controlled through the signals transferred in block 305. Low frequency pulses are derived from the interaction of the emissions from the primary and secondary arrays 200, 202.

In a block 307, low frequency pulsing of different points of the projected ultrasonic energy modifies the firing timing of the neurons in the human nervous system (in this example, the visual cortex 100), thereby giving rise to perceived sensory experiences, such as visual images. Sensory data is mapped in the neural cortex as differences in neural firing times. Thus, altering the firing times in cortical neurons can generate sensory experiences.

One advantage of the present system is that no surgery is needed to change neural activity causing a sensory experience.

Although the present invention has been described with reference to specific embodiments, these embodiments are illustrative only and not limiting. Many other applications of this present invention will be apparent in light of this disclosure and the following claims.

What is claimed is:

1. A non-invasive system for projecting sensory data in a part of a human brain, the system comprising:

a primary transducer array configured to emit acoustic energy as a coherent signal source toward the human brain;

a secondary transducer array positioned between the primary transducer array and the human brain; and a sensory data processing system coupled to the secondary transducer array, wherein the sensory data processing system sends an acoustical pattern signal to the secondary transducer array, the secondary transducer array producing a diffraction pattern for the emitted energy from the primary transducer array, the diffraction pattern altering neural firing timing in the brain.

2. The system of claim 1, wherein the primary and secondary transducer arrays are separated by a distance substantially equal to the wavelength of the emitted energy from the primary array.

3. The system of claim 1, wherein the primary and secondary transducer arrays are separated by a distance substantially equal to a multiple of the wavelength of the emissions from the primary array.

4. The system of claim 1, wherein the primary transducer array appears to the secondary transducer array as a coherent signal source.

5. The system of claim 1, wherein emitted energy from the secondary transducer array is amplitude and phase shifted from the emitted energy from the primary array.

6. The system of claim 1, wherein an interaction of emitted energies from the primary and secondary transducer arrays produces an interference pattern, which is projected into the human brain.

7. The system of claim 1, wherein an interaction of emitted energies from the primary and secondary transducer arrays produces a plurality of controllable, low frequency pulses.

8. The system of claim 1, wherein the primary transducer array comprises an array of piezoelectric elements.

9. The system of claim 1, wherein the secondary transducer array comprises an array of piezoelectric elements.

10. The system of claim 1, wherein the primary and secondary arrays comprise a plurality of piezoelectric elements that are held together by a flexible material, wherein the primary and secondary arrays may conform to a shape of the human head.

11. The system of claim 1, wherein the sensory data processing system obtains sensory data from a data source selected from a group consisting of a video camera, a VCR, a DVD player, a cable broadcast, a satellite broadcast, and an Internet connector.

12. The system of claim 1, wherein the sensory data processing system comprises a processing module configured to convert analog data from a data source to digital data for the secondary transducer array.

13. The system of claim 1, wherein the sensory data processing system converts sensory data to a plurality of neural firing time differences, and converts the neural firing time differences to an acoustical pattern signal, which is sent to the secondary transducer array.

14. The system of claim 1, wherein the sensory data processing system comprises:

a signal generator coupled to the secondary transducer array, the signal generator generating an acoustical pattern signal to the secondary transducer array, the acoustical pattern signal being based on sensory data from a sensory data source; and a reference signal generator coupled to the primary transducer array, the reference signal generator generating a reference signal to the primary transducer array.

\* \* \* \* \*